US006746456B2

United States Patent
Xiao

(10) Patent No.: US 6,746,456 B2
(45) Date of Patent: Jun. 8, 2004

(54) NEEDLE ARRAY SUTURING/SEWING ANASTOMOSIS DEVICE AND METHOD FOR ANASTOMOSIS

(75) Inventor: Jia Hua Xiao, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/967,639

(22) Filed: Sep. 28, 2001

(65) Prior Publication Data

US 2003/0065336 A1 Apr. 3, 2003

(51) Int. Cl.[7] ........................ A61B 17/04; A61B 17/12; A61B 17/08; A61B 17/06
(52) U.S. Cl. ...................... 606/144; 606/148; 606/153; 606/222
(58) Field of Search ................................ 606/144, 147, 606/139, 145, 222–227, 153; 112/163, 164, 165, 166, 167

(56) References Cited

U.S. PATENT DOCUMENTS

| 3,019,789 A | | 2/1962 | Whitehill et al. | |
|---|---|---|---|---|
| 4,593,693 A | | 6/1986 | Schenck et al. | |
| 4,803,984 A | | 2/1989 | Narayanan et al. | |
| 5,330,488 A | * | 7/1994 | Goldrath | 606/148 |
| 5,474,565 A | * | 12/1995 | Trott | 606/144 |
| 5,695,504 A | | 12/1997 | Gifford, III et al. | |
| 5,722,981 A | * | 3/1998 | Stevens | 606/148 |
| 5,843,126 A | * | 12/1998 | Jameel | 606/220 |
| 5,868,763 A | | 2/1999 | Spence et al. | |
| 5,901,655 A | * | 5/1999 | Sadasue | 112/162 |
| 5,904,697 A | | 5/1999 | Gifford, III et al. | |
| 5,976,159 A | | 11/1999 | Bolduc et al. | |
| 6,159,224 A | * | 12/2000 | Yoon | 606/147 |
| 6,170,415 B1 | * | 1/2001 | Inoue et al. | 112/163 |
| 6,187,019 B1 | * | 2/2001 | Stefanchik et al. | 606/144 |
| 6,247,419 B1 | * | 6/2001 | Tajima et al. | 112/98 |
| 2002/0198543 A1 | * | 12/2002 | Burdulis et al. | 606/144 |

FOREIGN PATENT DOCUMENTS

WO    WO 91/00060    * 1/1991 ................. 606/220

OTHER PUBLICATIONS

Harris, "How Sewing Machines Work" Copyright 1999 disclosure of sewing machines work.*

* cited by examiner

Primary Examiner—Michael J. Milano
Assistant Examiner—P Roberts

(57) ABSTRACT

A needle array adapted to deliver sutures for the anastomosis of two separated tissues through the intermediary of suturing and sewing. More particularly, provided is needle array delivering sutures for the side-to-side anastomosis of two separated vessels, such as an artery or body lumen and a vessel graft or the like. A method of utilizing a needle array is shown, which will provide sutures for sewing separated tissues together, and especially facilitates the side-to-side anastomosis of body lumens or vessels.

14 Claims, 1 Drawing Sheet

NEEDLE ARRAY SUTURING/SEWING ANASTOMOSIS DEVICE AND METHOD FOR ANASTOMOSIS

BACKGROUND OF THE INVENTION

1. Field of the Invention

The present invention relates to a needle array adapted to deliver sutures for the anastomosis of two separated tissues through the intermediary of suturing and sewing, and more particularly pertains to a novel needle array delivering sutures for the side-to-side anastomosis of two separated vessels, such as an artery or body lumen and a vessel graft or the like. Moreover, the invention is directed to a novel method of utilizing a needle array which will provide sutures for sewing separated tissues together, and especially facilitates the side-to-side anastomosis of body lumens or vessels.

The concept of anastomosis or the joining through the sewing or suturing of body vessels is widely known in the medical art. In particular, in order to suture or anastomotize two vessels, a single needle or hook element having a suture attached thereto is passed through the intimal tissue of the body vessels or grafts at specified locations, and the suture is then tightened and knotted so as to provide a closed connection between the adjoining tissues of the two body vessels. This procedure is then continually repeated by means of multiple needle passes until the required vessel/graft connection is completed.

The difficulties which are encountered in implementing the foregoing reside in that the use of individual needles, of necessity requires an extensive period of time in the implementation of the suturing and sewing process, this, in turn, increasing the risk of complication to a patient and with the attendant potential of morbidity and difficulty in healing of the sutured location.

In essence, as described by the present state-of-the medical technology which is concerned with the use of individual needles and thereto attached sutures in order to implement and complete anastomosis between body vessels and/or grafts, either multiple passes of the needle and suture are required, or it is necessary to effectuate a movement of the object which is being subjected to anastomosis, such as the grafts and/or body vessels, which to a considerable extent increase the difficulties in healing, causing pain and discomfort to the patient; while possibly enhance of the risk of morbidity or even mortality.

2. Discussion of the Prior Art

For instance, among various publications which relate to the implementation of anastomosis, is the use of a microsurgery tool as described in Narayanan et al. U.S. Pat. No. 4,803,984. However, this only provides for a single suture with a needle attached thereto puncturing through the tissue of adjacent vessel wherein the suturing is implemented in an end-to-end anastomosis. Basically, a large number of needle passes is required in order to extend about the circumferentially aligned ends of the adjoining vessels which, in effect is an extremely lengthy and difficult procedure subject to potential pain and physical harm to a patient.

Other aspects in implementing anastomosis reside in the use of clamps, such as disclosed in Schenck U.S. Pat. No. 4,593,693 in order to interengage the tissue of adjoining vessels and grafts.

Similarly, Bolduc et al. U.S Pat. No. 5,976,159 discloses anastomosis through the implementation of surgical clips which are adapted to engage adjacent vessels or body lumens in various mutual orientations, such as would facilitate side-to-side anastomosis procedures.

Other publications relate to the implementation of anastomosis by the use of various means, such as through clips or various types of clamps intended to interconnect body vessels. For example, such publications are Whitehill et al. U.S. Pat. No. 3,019,789; Gifford III et al. U.S. Pat. Nos. 5,695,504 and 5,904,697; and Spence et al. U.S. Pat. No. 5,868,763.

SUMMARY OF THE INVENTION

In order to overcome the limitations and shortcomings of the prior art in the suturing of tissues of separated body vessels and/or grafts in preferably side-to-side anastomosis, pursuant to the invention there is provided a needle array which in a concurrent mode is adapted to cause the needle array with an attached suture pass through the tissue of two superimposed vessels. The array of needles is provided with a single suture which is formed in a loop configuration extending over the tip of each needle such that the leading ends of the loops project beyond the punctured tissues. The needles are notched to enable a further suture to be passed through collectively each of the loops and the needles are then withdrawn leaving the sutures interengaged. Thereafter the sutures are tightened to draw the tissues of the vessels together and knotted so as to complete the entire anastomosis in essentially a single operative step.

Accordingly, it is an object of the present invention to provide a novel needle and suture array whereby a plurality of needles collectively bearing a single suture in a plurality of loops are adapted to concurrently pierce through the tissues of separated vessels and/or grafts and whereby a further suture is passed through the collective loops and the needle array retracted therefrom so as to enable the sutures to tighten the tissues together and then are knotted to anastomotize the vessels.

Another object of the present invention resides in a novel method of suturing two separated body vessels and/or grafts by passing concurrently a plurality of needles and a looped suture supported thereon in an array through the tissues of the vessels, forming a succession of suture loops through which a further suture is then passed, whereupon the needles are withdrawn, and the sutures are tightened and knotted to provide the required anastomosis of the body vessels or lumens in essentially a single operation.

BRIEF DESCRIPTION OF THE ACCOMPANYING DRAWINGS

Reference may now be made to the following detailed description of preferred embodiments of the invention, taken in conjunction with the accompanying drawings; in which:

FIG. 1 illustrates a diagrammatic transverse cross-section through two hollow or body vessels, such as an artery and a superimposed graft which have been cut in preparation for side-to-side anastonosis and are to revert to their interconnected flow position and fixed thereto;

FIG. 2 diagrammatically illustrates the tissue portions of the two vessels having a suturing needle array positioned adjacent thereto along the longitudinal extent thereof prior to suturing;

DETAILED DESCRIPTION OF PREFERED EMBODIMENTS

Figure 1:
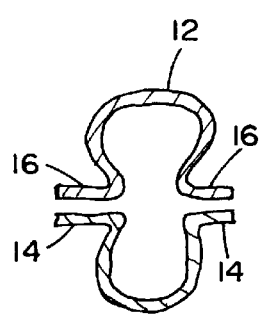

Referring in particular to FIG. 1, there is illustrated generally diagrammatically a transverse cross-section of a pair of vessels in the form of an artery 10 and a graft 12 which are being cut so as to communicate in a fluid or blood flow relationship, and which are to revert to the interconnected position and fixed thereto. In that instance, the vessels comprise an artery and graft which is to be attached thereto in a side-to-side anastomosis through the inventive suturing and sewing arrangement and method. Each of the vessel tissues have lip or flange portions 14, 16 which are to be superimposed and joined by suturing in a side-to-side anastomosis.

Figure 2:
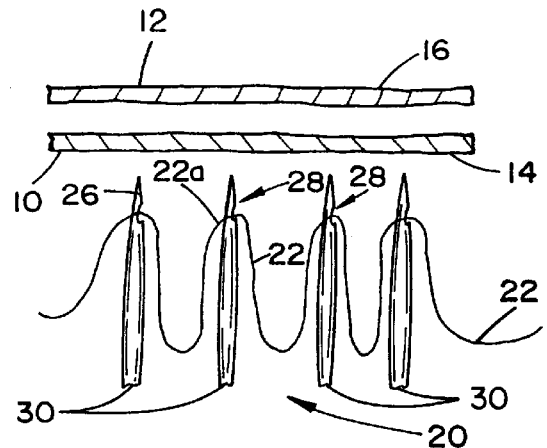

As shown in FIG. 2 of the drawings which illustrate a longitudinal view of the lip or tissue portions 14,16 of the superimposed vessels 10,12 which although as being shown separated are actually in face-to-face contact by being clamped at the ends thereof through clamping structure (not shown) so as to cause the vessels 10, 12 to be essentially immobilized. An array of suturing needles 20, which are aligned with the flanges 14,16; and wherein another array of needles may be located on opposite sides of the vessels, has a continuous single suture 22 positioned so as to be arranged thereover in a continuous pattern forming depending loops 22a, extending over the tip 26 of each respective needle 30. Each of the needles at the tip portion 26 thereof may have a notch 28 formed therein, so as to support the apex of each therewith associated loop of the suture 22.

Moreover, the notch of each needle 30 of the array of needles 20 has a groove or recess 28 formed in one side thereof at locations along the needle shanks somewhat below the tip 26 of each needle, and which are in an alignment with each other. The needles 30 of the needle array 20 are fixed relative to each other, and if desired may be provided in or mounted on a cartridge (not shown).

Figure 3:
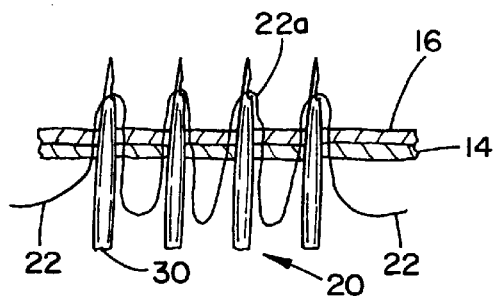
FIG. 3 illustrates the needle array having been pushed through the superimposed tissue portions of the tissue with the common suture thereon forming a plurality of loops.

As shown in FIG. 3, the needles 30 of the suturing needle array 20 with the continuous suture 22 having the loops 22a supported on each of the needle tips 26 are pushed simultaneously by suitable means (not shown) so as to pierce through the superimposed tissue flange portions 14,16 such that the needle tips 26 with the loops 22a of the suture 22 pierce through both tissue flanges 14,16

Figure 4:
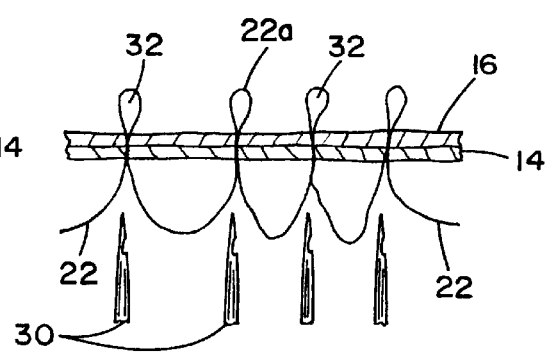
FIG. 4 illustrates the needles having been pulled back so as to provide a space within each loop through which a second suture will be interleaved.
Figure 5:
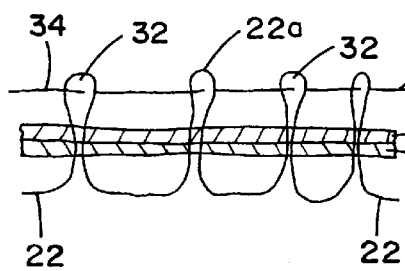
FIG. 5 illustrates the needles having been fully withdrawn from the tissues and leaving the interleaved sutures positioned therein.

Thereafter, as shown diagrammatically in FIG. 4 of the drawings, the needle array 20 is pulled back so as to form an outward bulge or space 32 in the protruding loops 22a of suture 22. A second suture 34 is then passed through the suture loops space 32 formed on each needle 30 of the needle array 20, as shown in FIG. 5.

The needle array 20, is then withdrawn from the tissue 14,16 leaving the suture loops 22a engaged with suture 34 along the upper surface of the tissue 14 of the graft 12, or the other vessels 10 depending upon orientation, and with the continuous first suture 22 having its straight portion 22b extending along the other surface of the joined tissues 14, 16.

Figure 6:
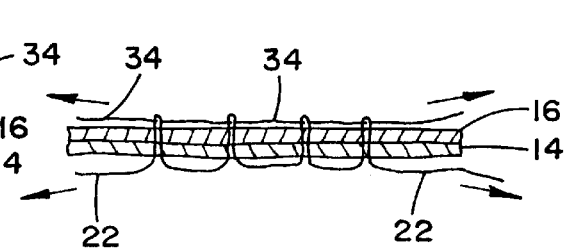
FIG. 6 illustrates the tissues having been anastomosized by the sutures being tightened and knotted in order to provide the required side-to-side anastomosis of the artery and graft.

Finally, as illustrated in FIG. 6 of the drawings, the opposite ends of each of the sutures 22 and 34 are pulled coaxially outwardly in the opposite directions of the arrows A so as to tighten the surface contact between the tissue portions 14, 16 of each of the vessels, and then the sutures 22, 34 are knotted together, as is well known in the medical art, so as to provide a permanent sutured side-to-side anastomosis extending along the length of the joined vessels 10,12.

Figure 7:
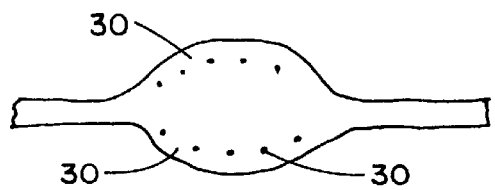
FIG. 7 illustrates a schematic view of a further possible configuration of a needle and suture array.

Although the suturing needle array 20 is illustrated as being in a linear array, and whereby the entire needle array may be attached to or mounted on a cartridge for easy and convenient handling, the needles 30 can also be arranged in an outwardly or convexly curved or circular array as shown in FIG. 7 of the drawing so as to enable an end-to-side anastomosis of a ring-shaped or stent shaped configuration utilizing essentially the same concept as hereinabove with regard to the side-to-side anastomosis of superimposed body vessels and grafts.

From the foregoing it becomes clearly evident that the present invention is directed to a simple arrangement and method of joining body vessel tissue in side-to-side anastomosis without the necessity for multiple passages of a needle through the tissue of body vessels/grafts in order to join portions thereof or having to move the vessels in relation to the needles and sutures.

While the invention has been particularly shown and described with respect to preferred embodiments thereof, it will be understood by those skilled in the art that the foregoing and other changes in form and details may be made therein without departing from the spirit and scope of the invention.

What is claimed is:

1. A method of implementing the anastomosis of two separated superimposed tissues from hollow superimposed body vessels through the intermediary of suturing and sewing; comprising the steps of:

(a) positioning an array of spaced suture needles along one side of said tissues wherein the tips of said needles face towards said tissues; a first continuous suture being supported on notch structure formed proximate each of said needle tips and forming depending loop portions extending along the shank portions of each of said needles;

(b) advancing said array of needles such that the needles tips co currently puncture through said superimposed tissues and cause said suture loops while supported on each of said notch structures to protrude through the opposite side of said superimposed tissues;

(c) retracting said needle array releasing said suture loops from said notch structures so as to form a space between each needle and a therewith a associated suture loop;

(d) passing a further continuous length of a second suture through each of the spaces between said loops so as to interleaf said first and second sutures; and (e) withdrawing said array of needles from said tissues, and tensioning and knotting together said first and second sutures so as to complete the anastomosis of said body vessels.

2. A method as claimed in claim 1, wherein said needle array extends linearly along the lengths of said superimposed tissues.

3. A method as claimed in claim 1, said further suture is pass through said spaces between said needles and suture loops.

4. A method as claimed in claim 1, wherein said suture loops are passed through said superimposed tissues in a single advance of said needles of said needle array.

5. A method as claimed in claim 1, wherein said needle array is mounted in a cartridge.

6. A method as claimed in claim 1, wherein a needle array is adapted to implement suturing on superimposed tissues on opposite edges of said body vessels a grafts.

7. A method as claimed in claim 1, wherein said needle array effectuates a side-to-side anastomosis of said superimposed tissues of the body vessels and grafts.

8. A device for implementing the anastomosis of two separated superimposed tissues from hollow superimposed body vessels through the intermediary of suturing and sewing; comprising:

(a) an array of spaced suture needles positioned along one side of said tissues wherein the tips of said needles face towards said tissues; a first continuous suture being supported on notch structure formed proximate each f said needle tips and forming depending loop portions extending along the shank portions of each of said needles;

(b) said array of needles being advanceable such that the needles tips concurrently puncture through said superimposed tissues and cause said suture loops while supported on each of said notch structures to protrude through the opposite side of said superimposed tissues;

(c) said needle array being retractable for releasing said structure loops from said notch structures so as to form a space between each needle and a therewith associated suture loop;

(d) a further continuous length of a second suture extending through each of the spaces between said loops so as to interleaf said first and second sutures; and (e) said array of needles being withdrawable from said tissues, and tensioning and knotting together said first and second sutures so as to complete the anastomosis of said body vessels.

9. A device as claimed in claim 8, wherein said needle array extends linearly along the lengths of said superimposed tissues.

10. A device as claimed in claim 8, wherein said further suture is passed through said spaces between said needles and suture loops.

11. A device as claimed in claim 8, wherein said suture loops e passed through said superimposed tissues in a single advance of said needles of said needle array.

12. A device as claimed in claim 8, wherein said needle array is mounted in a cartridge.

13. A device as claimed in claim 8, wherein a needle array is adapted to implement suturing on superimposed tissues on opposite edges of said body vessels and grafts.

14. A device as claimed in claim 8, wherein said needle array effectuates a side-to-side anastomosis of said superimposed tissues of the body vessels and grafts.

* * * * *